United States Patent [19]

Gueyne et al.

[11] Patent Number: 4,927,952

[45] Date of Patent: May 22, 1990

[54] SILANOL CONDENSATION PRODUCTS

[75] Inventors: Jean Gueyne; Marie-Christine Seguin, both of Monte-Carlo, Monaco

[73] Assignee: Exsymol S.A.M., Monte Carlo, Monaco

[21] Appl. No.: 197,848

[22] Filed: May 24, 1988

[30] Foreign Application Priority Data

May 26, 1987 [FR] France .................................. 87 07371
Aug. 7, 1987 [FR] France .................................. 87 11262

[51] Int. Cl.$^5$ ................................................ C07F 7/10
[52] U.S. Cl. ..................................... 556/419; 556/418; 556/420
[58] Field of Search ......................... 556/418, 420, 419

[56] References Cited

U.S. PATENT DOCUMENTS

| | | | |
|---|---|---|---|
| 3,513,184 | 5/1970 | Brison et al. | 556/418 |
| 3,700,716 | 10/1972 | Berger et al. | 556/418 |
| 4,496,754 | 1/1985 | Kanner et al. | 556/420 |
| 4,511,727 | 4/1985 | Martin | 556/418 |

*Primary Examiner*—John Doll
*Assistant Examiner*—Stuart L. Hendrickson
*Attorney, Agent, or Firm*—Ostrolenk, Faber, Gerb & Soffen

[57] ABSTRACT

Product of condensation of a silanol or a silanol derivative, which comprises an Si atom carrying two organic radicals and two oxygen atoms connected to organic groups other than the radicals; at least one of these organic groups carries at least one NH and a $NH_2$.

9 Claims, No Drawings

SILANOL CONDENSATION PRODUCTS

The present invention relates to a new series of silanol condensation products and their derivatives; it relates more particularly to those products formed by the condensation of silanols with organic compounds, carrying at least one carboxylic function, which also have one or more hydroxyls and one or more aminio groups. They can comprise siloxanic groups in their molecule.

The usefulness of silanols, siloxanes and their various derivatives is well known. It is known for example that alkyl silanols, such as methyl silanetriol, and their salicylates have a very beneficial action on conjunctive tissues; they prevent sclerosis, stimulate the regeneration of tissue and ensure its stabilisation. Moreover, organic polysiloxanes are employed as additives for plastics materials, as they facilitate removal from moulds; they are also used for the lubrication of organic fibres and as emulsifiers and foaming agents.

The present invention provides an advance over the known art relating to organic compounds of silicon, in that it concerns condensation products which are highly stable to heat, which can be manipulated, transported and stored in the solid or oily state and not necessarily in solution, as are the products mentioned above. It is possible to have according to the invention compounds which hydrolyse or alcoholise in solution, thus giving products in the nascent state, which are particularly active. Very effective products having therapeutic and cosmetic action are obtained according to the invention with hydroxylated aminoacids.

The new products according to the invention, which comprise an Si atom carrying two organic radicals and two oxygen atoms connected to organic groups other than these radicals, are characterised in that at least one of these groups carries at least one $-NH_2$ or $=NH$ groups.

One of or the two organic groups of these products can be cyclic or together can form a ring.

The products according to the invention can be represented by the general formula:

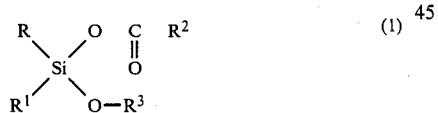

where the radicals R and $R^1$, the same or different, are aliphatic or aryl hydrocarbon or oxyhydrocarbon radicals; $R^2$ and $R^3$, the same or different between themselves or each different from R and $R^1$, are linear or cyclic organic groups at least one of which carries one or more $-NH_2$ or $=NH$ groups.

R and $R^1$ can in particular be alkyls or alkenyls, preferably from $C_1$ to $C_{18}$, benzene or naphthalene aryls which can carry substituents, in particular alkyls, halogens, hydroxyls, alkoxyls or acyls; they can be $C_1$ to $C_8$ alkoxy, benzene or naphthalene aryloxy, if required substituted as indicated above, or $C_4$ to $C_8$ cycloalkyls or cycloalkenyls.

Also $R^2$ and $R^3$ can be $C_1$ to $C_{18}$ alkyls or alkenyls, aryls, alkoxy, aryloxy, cycloalkyls or cycloalkenyls, defined as above, but different from R and $R^1$.

$R^2$ and $R^3$ can be connected to one another in which case they form a ring with the part

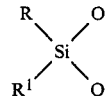

of the molecule. An important case is that where $R^2$ and $R^3$ together form a ring, for example having 5 or 6 elements.

When the products according to the invention are intended for biological uses, particularly as medicaments or in cosmetics, it is highly preferable for one of the radicals R and $R^1$ to be hydrocarbon namely alkyl, alkenyl or aryl, the second being of a different nature, in particular alkoxy, alkenoxy, aryloxy, hydroxy-alkyl or amino. It is in effect considered that the silanols and their derivatives, where the silicon atom carries more than one hydrocarbon radical connected to Si by a C-Si bond, have a lower efficacy than that of compounds having a single bond of this type.

This is the reason why those of the products according to the invention which are intended for pharmaceutical uses preferably correspond to the formula (1) in which R, as indicated above, can be a hydrocarbon or oxyhydrocarbon radical, while $R^1$ is never a hydrocarbon radical. In other words in this form of the invention, preferred for pharmaceutical products, in the part of the molecule

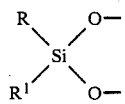

derived from a mono- alkyl, alkenyl- or aryl- (R) silane di- or tri-ol, $R^1$ can be a group of the type $R^4$O-(bond-O-Si) where $R^4$ is an alkyl, alkenyl, aryl, cycloalkyl, hydrogen, ether or polyether possibly hydroxylated, the group $R^4$O possibly being blocked for example with an acid molecule, $R^1$ can on the other hand comprise an amine or amide function possibly blocked.

Thus by way of purely illustrative examples, the formulae of the part

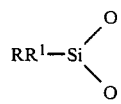

of some of the condensation products according to the invention particularly utilisable for pharmaceutical purposes are:

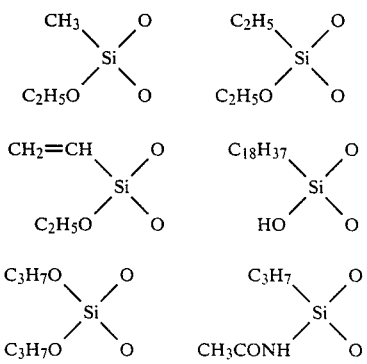

-continued

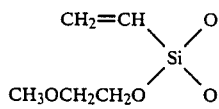

This example it will be understood has no limitative nature.

Products according to the invention of particular interest correspond to the general formula:

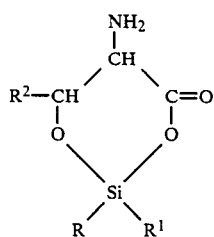

where each of R and $R^1$ same or different is a $C_1$ to $C_4$ alkyl or a $C_1$ to $C_4$ alkoxy group, while $R^2$ is H or a $C_1$ to $C_4$ alkyl.

The condensation products according to the invention can be prepared by the action of a silane, silanol or siloxane having at least reactive groups, with a carboxylic acid having an hydroxyl and an amino group, the reaction taking place within an anhydrous organic solvent in the presence of a neutraliser. The preparation is terminated by elimination of the solvent by boiling.

Another procedure, generally allowing the attainment of better yields, comprises reacting the active groups of the Si compound with a metal derivative of the carboxylic acid indicated above.

Silanes having at least two reactive groups are in particular the di- and tri-halides respectively of di- and mono-hydrocarbyl silicon, namely $R_2SiX_2$ and $RSiX_3$, R being a hydrocarbon radical and X a halogen. Such silanes are for example $(CH_3)_2SiCl_2$ and $CH_3SiCl_3$. However dihalogen compounds are more preferred, because of subsequent complications, namely the cross-linking polymerisation which can be caused by the third halogen.

Siloxanes utilisable in the process according to the invention are organosilicons of the $R'_2SiQ_2$ and $R'SiQ_3$ types, R' being a hydrocarbon or oxyhydrocarbon radical such as for example —$CH_3$ or $CH_3O$—, while Q is —OH or —OR, R indicating as above a hydrocarbon radical. Examples of such siloxanes, without any limitation are:

$(CH_3)_2Si(OH)_2$; $(C_2H_5)_2Si(OCH_3)_2$; $C_6H_5$—$Si(OC_2H_5)_3$; $C_4H_9O$—$Si(OH)_3$; $Si(OC_2H_5)_4$; $C_2H_5$—$Si(OH)_3$;

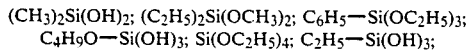 and the like

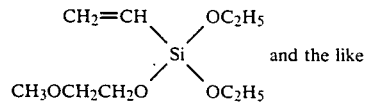

The compounds preferred for the process of the invention are those where R is a lower alkyl ($C_1$ to $C_4$) leading to the formation of the corresponding alcohol, easily separable by distillation.

As carboxylic acids to be condensed with the siloxane, various aliphatic or aryl acids can be used, including diacids carrying OH and $NH_2$ or NH functions.

These are in particular serine, diserine, threonine, hydroxyproline, tyrosine, casein or amino phenyl lactic acid.

By way of non-limitative examples, these two diagrams give an idea of the condensation reaction in the case of the invention:

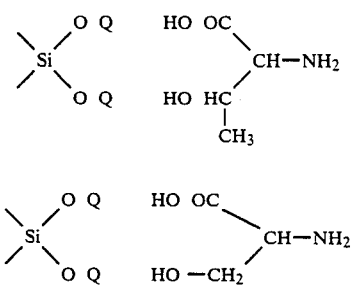

As regards anhydrous organic solvents employed in the preparation of the condensation products according to the invention, these are selected from liquids dissolving the silicon compound and the acid utilised and, preferbly, boiling at temperatures which do not exceed about 150° C. Thus these are liquids which do not react with the reactants present. Thus use can be made depending upon the case of aliphatic hydrocarbons particularly from $C_6$ to $C_{12}$, aromatics such as benzene, toluene, xylene etc, chlorinated solvents, terpenes, ethers such as dioxane, tetrahydrofuran etc. It is particularly practical to use as the solvent a silane or silanol, in particular the same one as is used for the reaction. As indicated for terminating the reaction by heating preferably between 50° and 100° C., this heating serves at the same time to eliminate the solvent and it is carried out under a pressure, possibly reduced, under which the solvent boils at an adequate temperature.

Naturalisers which are well known in the chemical art do not need to be mentioned here; reference is merely made to various amines for example trimethylamine, dibutylamine or pyridine which are utilisable in the process according to the invention.

The invention is illustrated by the non-limitative examples which follow:

EXAMPLE 1

Condensation of the sodium salt of serine with dichloro dimethyl silane

Preparation of the sodium derivative of serine is first carried out by the action of Na ethanolate. For this, 0.2 atom of Na or 4.6 g is reacted with 200 ml of absolute ethanol in an ice bath; when all the sodium is dissolved, the solution of Na ethanolate obtained is removed from the ice bath and then 0.1 mole or 10.5 g of serine is added. After ½ hour, a precipitate of the sodium derivative appears. The ethanol is then distilled to dryness in order to obtain a white powder formed by the Na salt of serine.

This powder is put into suspension in chloroform and then 0.1 mol, namely 12.9 g of $Cl_2Si(CH_3)_2$ is added and the whole is boiled under reflux for 24 hours which produces the reaction:

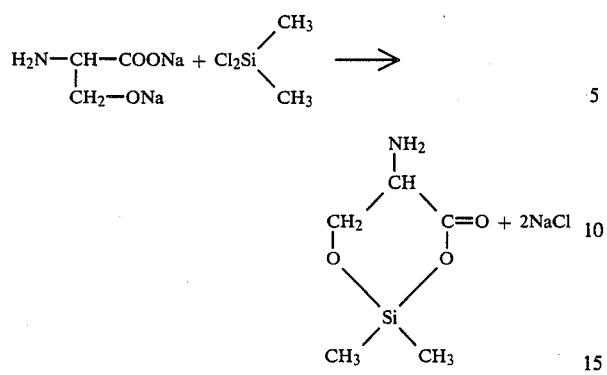

The condensate is obtained in a yield of 97% with respect to the serine used, after separation by filtration of the precipitate of NaCl and rinsing with chloroform. The solid product so prepared has the following characteristics:

| | IR | | NMR $^1$H | |
|---|---|---|---|---|
| C=O | 1720 cm$^{-1}$ | | CH$_3$—Si | 0,38 ppm singulet |
| CH$_3$—Si | 800 cm$^{-1}$ | 1260 cm$^{-1}$ | CH—N | 4,52 ppm triplet |
| NH$_2$ | 3220 cm$^{-1}$ | | CH$_2$—O | 3,20 ppm doublet |
| CH | 2900 cm$^{-1}$ | | NH$_2$ | 7,25 ppm multiplet |

EXAMPLE 2

Condensation of serine with Cl$_2$Si(CH$_3$)$_2$ in the presence of a neutraliser 0.1 mole of serine is put into suspension in 200 ml of CH$_2$Cl$_2$ to which is added 0.2 mole of triethylamine. Then there is added drop by drop 0.11 mole of dichlorodimethylsilane. The mixture is taken to reflux in the solvent for 12 hours and then allowed to return to the ambient temperature. The reaction mixture is filtered, the precipitate formed is washed with dichloromethane and then dried under reduced pressure. The solid product obtained in a yield of 71% over the serine corresponds to the cyclic siloxane according to the reaction scheme:

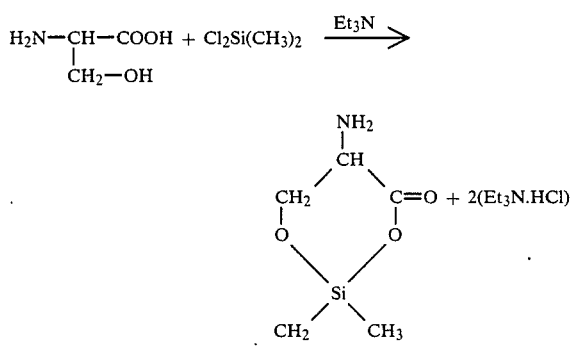

The characteristics of this condensate are partically the same for those of Example 1:

| | IR | | NMR $^1$H | |
|---|---|---|---|---|
| C=O | 1730 cm$^{-1}$ | | CH$_3$—Si | 0,35 ppm |
| CH$_3$—Si | 815 cm$^{-1}$,1260 cm$^{-1}$ | | CH—N | 4,52 ppm singulet triplet |
| NH$_2$ | 3200 cm$^{-1}$ | | CH$_2$—O | 3,25 ppm doublet |
| | | | NH$_2$ | 7,3 ppm multiplet |

EXAMPLE 3

Product of condensation of a monoalkyl trialkoxy silane with an amino acid alcohol the NH$_2$ function of which is protected by acetylation.

According to the mode of operation of Example 2, mono-methyl triethoxy silane is reacted with acetyl serine. The reaction can be written:

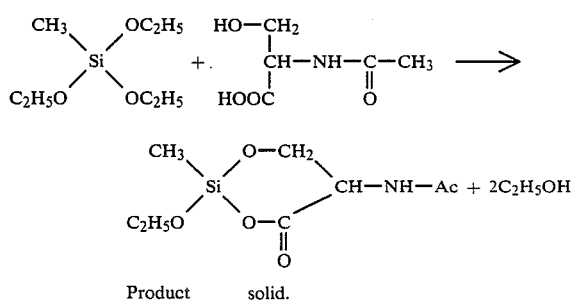

Product solid.

EXAMPLE 4

Another aminated condensation product according to the invention. Preparation according to Example 3 with acetyl-threonine in place of serine:

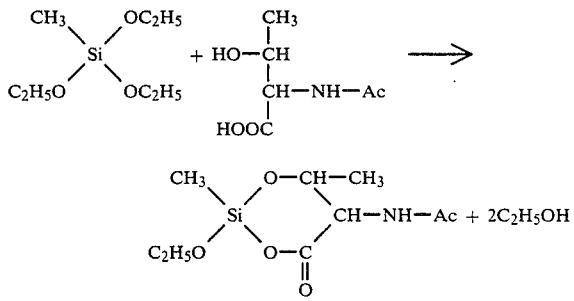

EXAMPLE 5

Condensation of a silanol with an aromatic amino-acid having a phenol function.

To a solution of 1 mole of acetyl-tyrosine

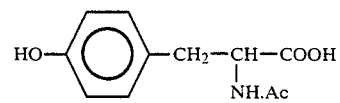

in 500 ml of benzene, 100 ml of pyridine, 100 ml of ethyl acetate and 1.5 mole of CH$_3$-Si(OC$_2$H$_5$)$_3$ or 267 g (300 ml) are added. The solvent is slowly distilled under atmospheric pressure. Then by distillation under vacuum, 338 g of an oil is recovered which is dissolved in ethyl acetate; the solution is passed through a silica column which is then eluated with a mixture of 60 vol. ethyl acetate and 40 vol. ethyl ether. Evaporation of the eluate leaves a yellow solid of the following characteristics:

| M. P. ≃ 62° C. | IR: 3300-2900-1730-1630-1050-920-780 |
|---|---|
| | NMR: 6,8 ppm multiplet 4H |
| | 4,5 ppm multiplet 1H |
| | 2,3 ppm multiplet 2H |
| | 1,9 ppm singulet 3H |
| | 0,3 ppm singulet 3H |

The formula indicated for this compound is:

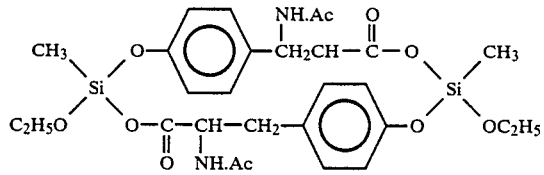

EXAMPLE 6

Following the technique of Example 1, a condensation was effected according to the reaction:

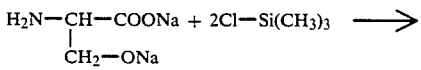

(sodium derivative of serine)

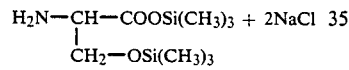

The solid product obtained in a yield of 96% has the following characteristics.

| | IR | NMR $^1$H | |
|---|---|---|---|
| C=O | 1730 cm$^{-1}$ | (CH$_3$)$_3$—Si | 0,39 ppm, singulet relative integration 18 |
| Si—O—C | 1090 cm$^{-1}$ | NH$_2$ | 7,2 ppm, multiplet relative integration 2 |
| CH$_3$—Si | 800 cm$^{-1}$, 1250 cm$^{-1}$ | CH—N | 4,5 ppm, triplet relative integration 1 |
| NH$_2$ | 3200 cm$^{-1}$ | CH$_2$—O | 3,2 ppm, doublet relative integration 2 |

It can be seen that the process of the invention allows the preparation of the desired compound with a free NH$_2$ group in a very good yield.

EXAMPLE 7

In a manner analogous to that of Example 1, the condensation is effected:

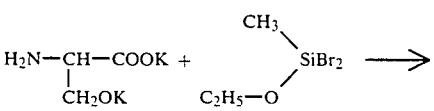

(potassium derivative of serine)

-continued

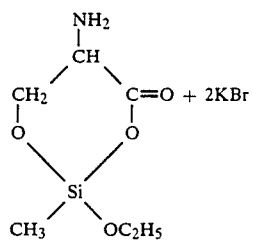

The new solid compound has the following characteristics:

| IR | | NMR | |
|---|---|---|---|
| C=O | 1730 cm$^{-1}$ | CH$_3$—Si | 0,35 ppm singulet |
| CH$_3$—Si | 780 cm$^{-1}$ 1265 cm$^{-1}$ | CH—N | 4,52 ppm triplet |
| NH$_2$ | 3200 cm$^{-1}$ | CH$_2$—O | 3,20 ppm doublet |
| CH— | 2950 cm$^{-1}$ | Et-O CH$_3$ | 1,25 ppm triplet |
| | | CH$_2$ | 3,75 ppm quadruplet |
| | | NH$_2$ | 7,40 ppm |

EXAMPLE 8

Condensation of threonine with a silanol

The mode of operation of Example 1 is used for the reaction:

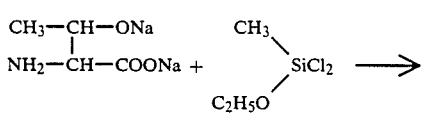

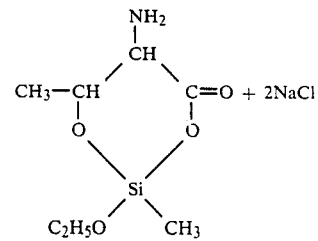

The product obtained with a yield of 95% is solid and has the following characteristics:

| IR | | NMR | |
|---|---|---|---|
| C=O | 1720 cm$^{-1}$ | CH$_3$—CH | 1,5 ppm doublet |
| CH$_3$—Si | 800 cm$^{-1}$, 1260 cm$^{-1}$ | Me—CH—C $\;\;\;\;\;\;\;\;\;\;$ O | 3,10 ppm multiplet (8 beams) |
| NH$_2$ | 3200 cm$^{-1}$ | | |
| C—H | 2900 cm$^{-1}$ | CH—N | 4,42 ppm doublet |
| | | CH$_3$—CH$_2$—O | 1,25 ppm triplet CH$_3$ 3,75 ppm quatruplet CH$_1$ |
| | | CH$_3$—Si | 0,35 ppm singulet |

EXAMPLE 9

The technique of the preceding examples is applied to the condensation of the sodium derivative of threonine with dichloro dimethyl silane. Thus the following reaction is carried out:

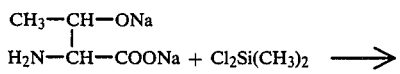

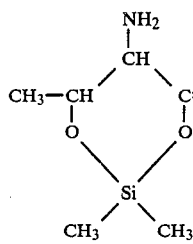

The solid product formed is obtained in a yield of 96%; it has the characteristics:

| | IR | | NMR |
|---|---|---|---|
| C=O | 1750 cm$^{-1}$ | CH$_3$—CH | 1,5 ppm doublet |
| CH$_3$—Si | 790 cm$^{-1}$, 1250 cm$^{-1}$ | Me—CH $\mid$ O | 3,05 ppm multiplet |
| NH$_2$ | 3200 cm$^{-1}$ | | |
| CH | 2900 cm$^{-1}$ | CH—N CH$_3$—Si | 4,42 ppm doublet 0,38 ppm singulet |

We claim:

1. A compound of the formula:

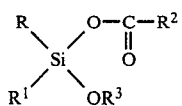

wherein: R and R$^1$ are alkyl groups, alkenyl groups, alkoxy groups, cycloalkyl groups, hydrocarbon aryl groups, unsubstituted or substituted with halogen, hydroxyl, acyl or alkoxy groups, or amide groups of up to 18 carbon atoms or hydroxy; R$^2$ and R$^3$ independently are alkyl groups, alkenyl groups, alkoxy groups, cycloalkyl groups, cycloalkenyl groups, hydrocarbon aryl groups or aryloxy groups of up to 18 carbon atoms or are linked to form a ring; and wherein at least one of the R$^2$ and R$^3$ groups contain an NH$_2$ or NH moiety.

2. The compound of claim 1, wherein said hydrocarbon aryl groups R and R$^1$ are substituted with at least one moiety selected from the group consisting of halogen, hydroxyl groups, alkoxyl groups and acyl groups.

3. The compound of claim 1, containing an amide moiety in R$^2$ or R$^3$.

4. The compound of claim 1, wherein R and R$^1$ are alkyl groups having 1 to 8 carbon atoms or alkoxy groups having 1 to 8 carbon atoms.

5. The compound of claim 1, wherein R$^2$ and R$^3$ are alkyl groups having 1 or 2 carbon atoms or alkenyl groups having 1 or 2 carbon atoms.

6. The compound of claim 1, wherein R$^2$ and R$^3$ are linked to complete a 5 or 6 membered ring.

7. The compound of claim 6 of the formula:

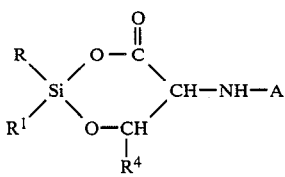

wherein A is hydrogen or acetyl and R$^4$ is hydrogen or an alkyl group having 1 to 4 carbon atoms.

8. The compound of claim 7, wherein R and R$^1$ are alkyl or alkoxy of 1 to 4 carbon atoms.

9. The compound of claim 1, wherein R$^1$ is not a hydrocarbon group.

* * * * *